(12) United States Patent
Mosenson et al.

(10) Patent No.: US 6,494,391 B2
(45) Date of Patent: Dec. 17, 2002

(54) APPARATUS FOR TREATING WASTE, PARTICULARLY MEDICAL WASTE, TO FACILITATE ITS DISPOSITION

(75) Inventors: Benjamin Mosenson, Tivon (IL); Yuri Litinsky, Afula (IL); Ilan Mark, Gilboa (IL)

(73) Assignee: M.C.M. Environmental Technologies Ltd., Doarna Gilboa (IL)

( * ) Notice: Subject to any disclaimer, the term of this patent is extended or adjusted under 35 U.S.C. 154(b) by 34 days.

(21) Appl. No.: 09/824,685

(22) Filed: Apr. 4, 2001

(65) Prior Publication Data

US 2002/0145063 A1 Oct. 10, 2002

Related U.S. Application Data

(60) Provisional application No. 60/265,870, filed on Feb. 5, 2001.

(51) Int. Cl.[7] ................................................. B02C 19/12
(52) U.S. Cl. .................. 241/36; 241/38; 241/101.2; 241/285.2; 241/606
(58) Field of Search ........................ 241/285.1, 285.2, 241/100, 101.2, 606, 38, 57, 36

(56) References Cited

U.S. PATENT DOCUMENTS

| | | | | |
|---|---|---|---|---|
| 3,589,276 A | * | 6/1971 | Swallert | 100/104 |
| 4,984,748 A | * | 1/1991 | Kimura | 241/100 |
| 5,273,221 A | * | 12/1993 | McCarthy | 206/366 |
| 5,620,654 A | | 4/1997 | Mosenson | |
| 5,673,861 A | | 10/1997 | Miller | |

\* cited by examiner

Primary Examiner—Mark Rosenbaum
(74) Attorney, Agent, or Firm—G.E. Ehrlich Ltd.

(57) ABSTRACT

Apparatus for treating waste, particularly all types of medical waste, to facilitate its disposition includes a treatment vessel having an open top pivotal within a housing to a waste-loading position with its open top aligned with the housing inlet for receiving the waste, a waste-treating position for shredding the waste by a shredder unit disposed within the treatment vessel, and a waste-removing position with its open top aligned with the housing outlet for removing the shredded waste. The apparatus further include a compactor head for compacting the waste within the treatment vessel, a water feed line, and a disinfectant feed line, for feeding water and a disinfectant into the treatment vessel, for mixing with the waste while it is being compacted and shredded.

20 Claims, 5 Drawing Sheets

APPARATUS FOR TREATING WASTE, PARTICULARLY MEDICAL WASTE, TO FACILITATE ITS DISPOSITION

RELATED APPLICATION

The present application is related to Provisional Application Serial No. 60/265,870, filed Feb. 5, 2001, the priority date of which is claimed herein, and the contents of which are incorporated herein by reference.

FIELD AND BACKGROUND OF THE INVENTION

The present invention relates to apparatus for treating waste to facilitate its disposition. The invention is particularly useful for treating medical waste of all types, and is therefore described below with respect to this application.

Waste in general, and medical waste in particular, present a number of disposal problems. Medical waste, as generated in medical, veterinary, dental and laboratory facilities, includes a wide variety of forms, such as bandages, gloves, infusion bags, hypodermic needles, syringes, products of dialysis, human and animal waste. Such waste must be disposed in a safe, expeditious and hazard-free manner. In large medical facilities, the medical waste is generally collected at a central location and disposed by incineration, grinding, and/or heating. Such processes are not only costly, but may also be environment-unfriendly in the odors generated or in the degradation of the environment.

Because of the different types of medical waste to be disposed, a number of devices have been developed which include shredders for shredding the medical waste in order to reduce the overall volume and to facilitate sterilization. Examples of apparatus of this type are described in U.S. Pat. No. 5,673,861 by Charles Miller, and in U.S. Pat. No. 5,620,654 by Beni Mosenson, one of the inventors in the present application. While the invention described in the latter patent has been incorporated in commercial apparatus, such an apparatus is relatively large and costly, and therefore has been found to be more suitable for relatively large medical facilities, such as large-size and medium-size hospitals, than for relatively small facilities, such as medical, dental, veterinary and dialysis clinics.

OBJECTS AND BRIEF SUMMARY OF THE INVENTION

An object of the present invention is to provide a relatively simple and compact apparatus for disposing of waste in general, and medical waste in particular, in a safe, expeditious and hazard-free manner. Another object of the invention is to provide such an apparatus particularly suitable for use by relatively small facilities such as medical, dental, dialysis and veterinary clinics.

According to one aspect of the present invention, there is provided apparatus for treating waste to facilitate its disposition, comprising: a housing having an inlet for introducing the waste to be treated; a treatment vessel within the housing and having an open top for receiving and removing the waste, the treatment vessel being pivotal to a waste-loading position with its open top aligned with the housing inlet for receiving waste introduced therethrough, and to a waste-treating position for treating the waste within the treatment vessel; and a shredder within the treatment vessel for shredding waste therein before being removed from the treatment vessel.

The term shredder, as used herein, is intended to include any device which shreds, grinds, or otherwise reduces the waste materials to small particles or pieces for disposal.

According to further features in the described preferred embodiments, the housing also has an outlet, separate from the inlet, for removing the waste after its treatment; and the treatment vessel is also pivotal to a waste-removing position with its open top aligned with the housing outlet for removing therethrough the waste after treatment in the treatment vessel.

According to further features in the described preferred embodiments, the shredder is driven by a drive within the housing and coupled to the shredder within the treatment vessel by a shaft passing through a side wall of the treatment vessel; the treatment vessel is pivotally mounted about the shaft.

According to further features in the described preferred embodiment, the apparatus further comprises: a compactor head aligned with the open end of the treatment vessel when the treatment vessel is in the waste-treating position so as to be reciprocatable within the treatment vessel to compact the waste therein; and a control system permitting operation of the compactor head only when the treatment vessel is in its waste-treating position. A water supply line feeds water into the treatment vessel to be mixed with the waste therein during the operation of the compactor head and shredder.

When the apparatus is to be used for disposing medical waste, the apparatus would further comprise a feed line for feeding a disinfectant into the treatment vessel to be mixed with the waste and the water during the operation of the compactor head. In one described preferred embodiment, the disinfectant is a liquid disinfectant fed into the treatment vessel via the compactor head so as to be mixed with the waste and the water within the treatment vessel during the operation of the compactor head. In another described preferred embodiment, the disinfectant is ozone which is fed directly into the treatment vessel during the operation of the compactor head.

According to further features in the described preferred embodiments, the housing outlet is occupied by a waste-removal drawer normally in an inner position aligned with the open end of the treatment vessel when the treatment vessel is in its waste-removing position to receive the waste therefrom, but is movable outwardly to enable removal of the waste from the drawer. Preferably, the waste-removal drawer has a bottom which is slanted downwardly from its outer side toward its inner side to permit liquid in the treated waste to separate from the solids and to drain to the inner side of the drawer. The drawer includes an outlet opening at its inner side to drain the liquid therefrom.

As will be described more particularly below, such apparatus provides a number of important advantages particularly making it suitable for use in small facilities for disposing medical waste. Since the complete treatment, from the introduction of the raw medical waste to its final disinfected and disposable form, is performed in a single treatment vessel, the handling of the medical waste is greatly simplified, and the chances of infecting handlers or equipment are greatly reduced. Since the treatment vessel in which the waste is treated is pivotally mounted to its various positions for loading, treating and removing the waste, the invention may be implemented in compact apparatus of relatively small size suitable for small offices and clinics. In addition, the provision of the compactor head, the water supply line, and the disinfectant feed line, enable the medical waste to be converted to a reduced-volume and disinfected form for disposable in a safe, expeditious and hazard-free manner.

Further features and advantages of the invention will be apparent from the description below.

DESCRIPTION OF PREFERRED EMBODIMENTS

The invention is herein described, by way of example only, with reference to the accompanying drawings, wherein.

DESCRIPTION OF PREFERRED EMBODIMENT
Overall Construction

Figure 1:
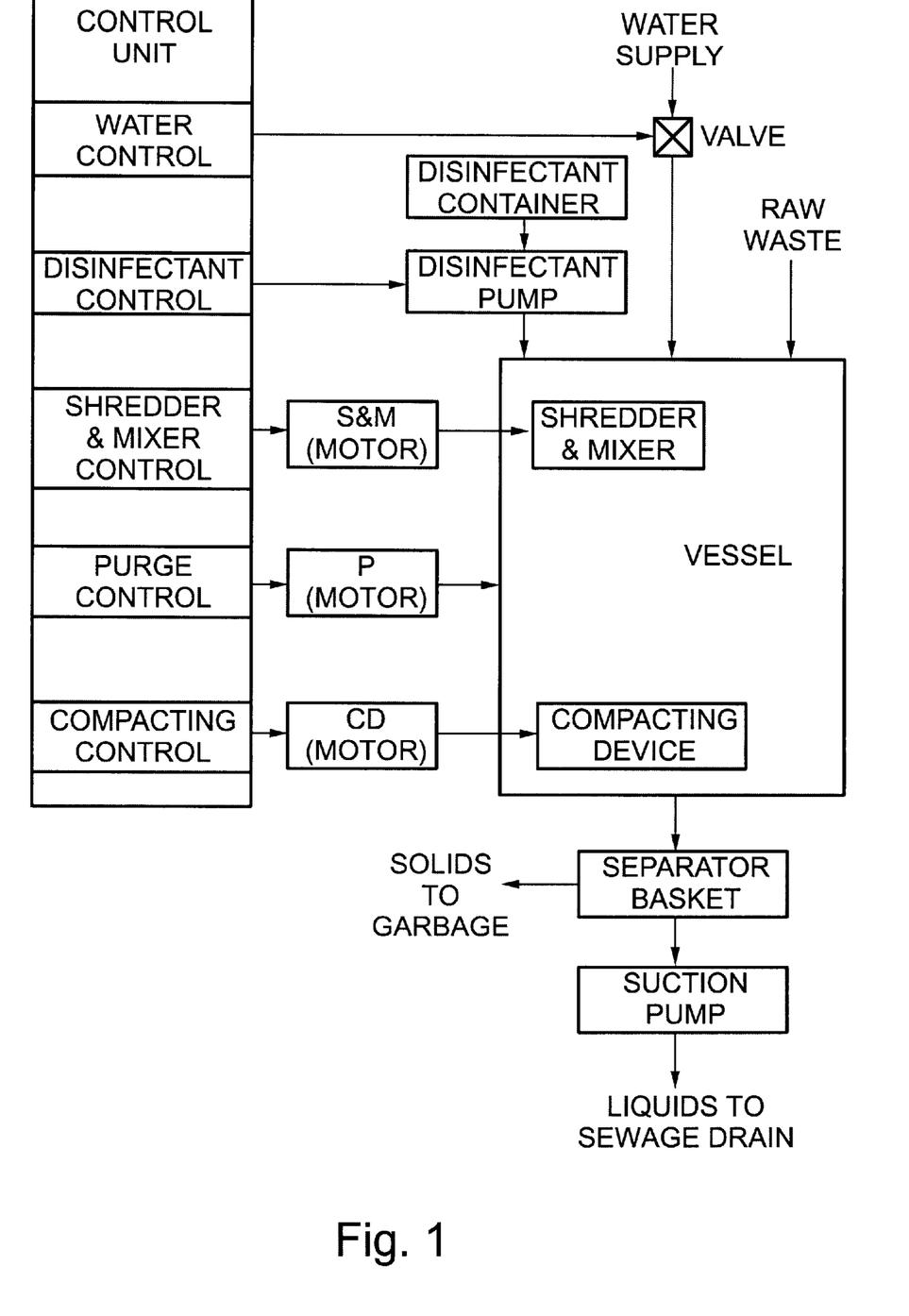
FIG. 1 is a block diagram schematically illustrating the functional components of one form of apparatus constructed in accordance with the present invention.

FIG. 1 is a functional block diagram illustrating the main functional components of the described apparatus. Such apparatus includes a housing (not shown in FIG. 1) enclosing a treatment vessel, generally designated 2, for receiving the raw medical waste and for converting it to a reduced-volume and disinfected form for disposition in a safe and hazard-free manner. A shredder 3 is provided within treatment vessel 2 and is driven by a shredder motor 4 externally of the treatment vessel. The apparatus further includes a compactor head 5 movable within the treatment vessel 2 and driven by a compactor motor 6 externally of the treatment vessel.

As will be described more particularly below, treatment vessel 2 is movable by a positioning drive 7 to a plurality of positions including: (1) a waste-loading position wherein it receives the raw medical waste introduced via the housing inlet (not shown in FIG. 1); (2) a waste-treating position wherein the shredder 3 is operated, together with the compactor head 5, to shred the waste and mix it with water fed into the treatment vessel under the control of a valve 8, and a disinfectant fed into the treatment vessel from a reservoir 9 via a disinfectant pump 10; and (3) a waste-removal position wherein the shredded and disinfected waste is collected in a collector 11 for removal, whereas the disinfected liquid is removed by a suction pump 12. All the foregoing operations are controlled, in the manner to be described below, by a control unit, generally designated 13 in FIG. 1.

Figure 2:
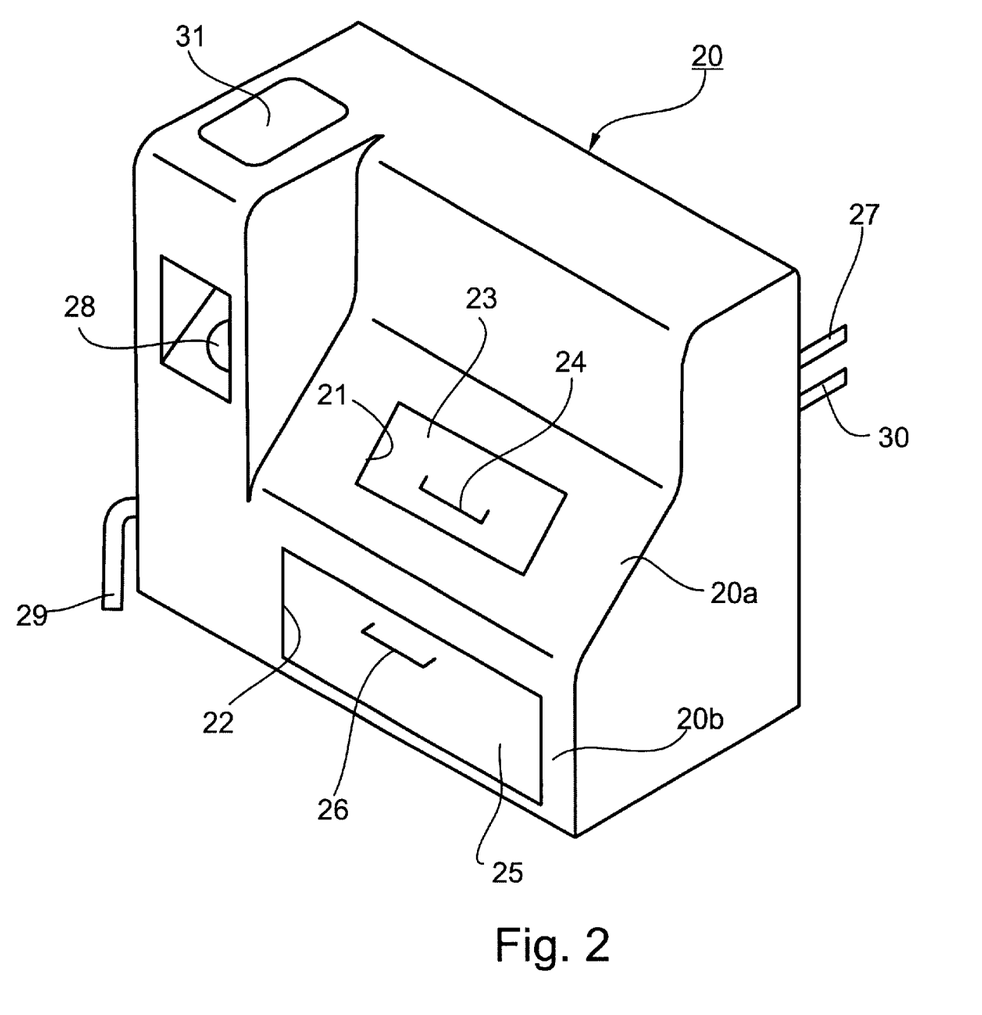
FIG. 2 is a three-dimensional view illustrating the external appearance of one form of apparatus constructed in accordance with the present invention.
Figure 3:
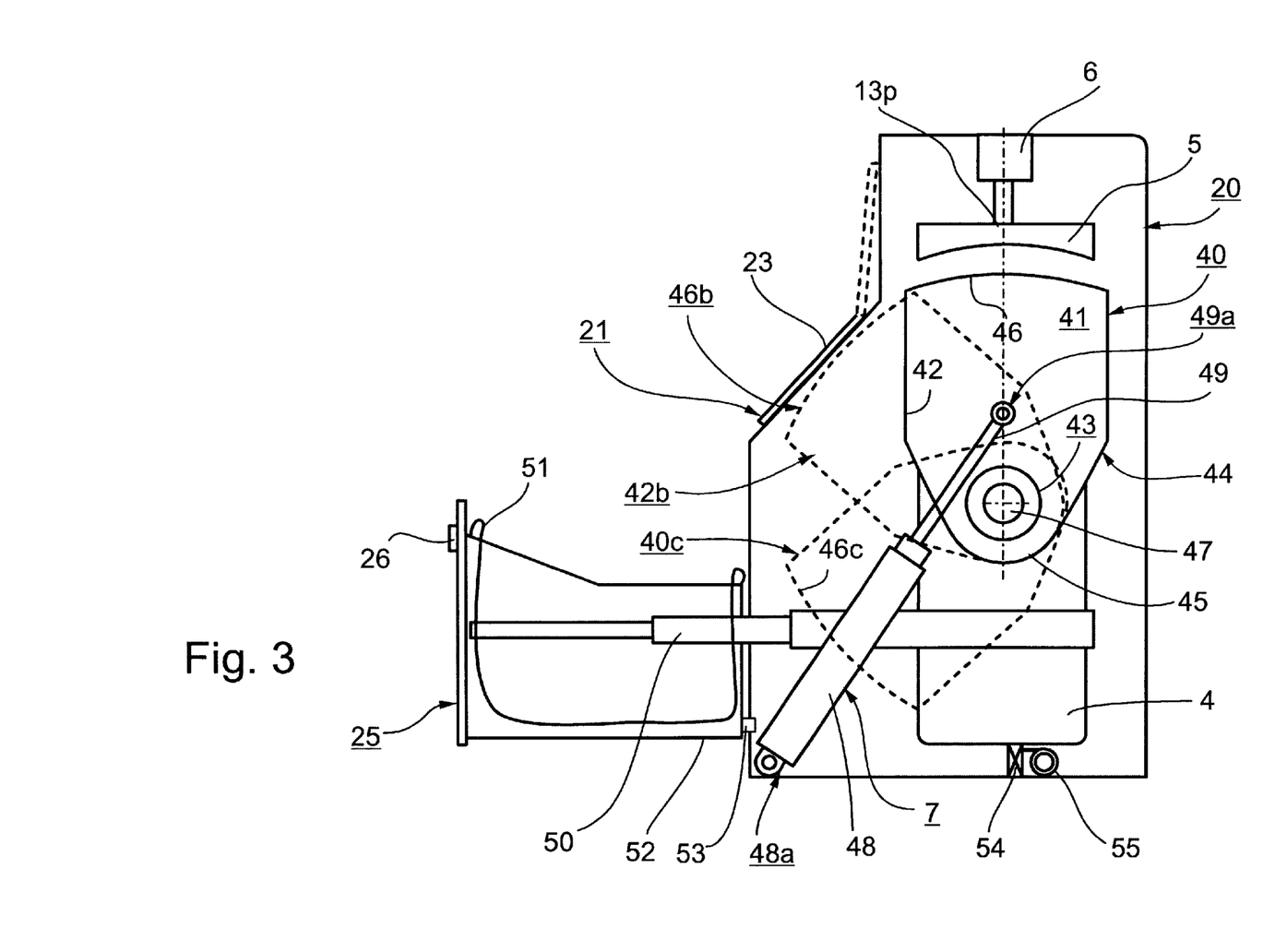
FIG. 3 is a side view diagrammatically illustrating the construction of the apparatus of FIG. 1, including the various positions of the treatment vessel for receiving, treating and removing the medical waste after treatment.
Figure 4:
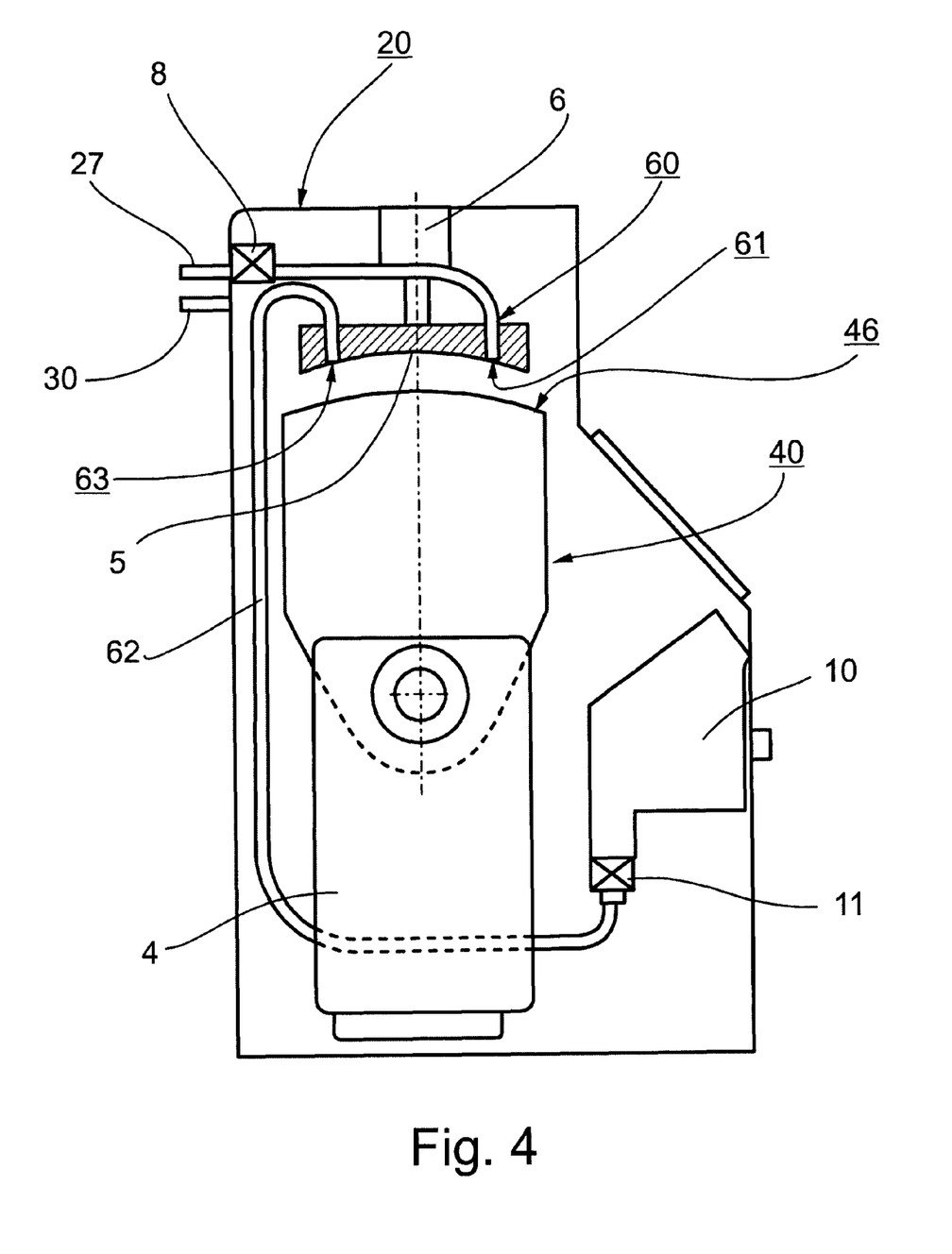
FIG. 4 diagrammatically illustrates the manner in which the medical waste is disinfected by a liquid disinfectant.

FIGS. 2–4 illustrate one construction of the apparatus in accordance with the invention as illustrated in the functional block diagram of FIG. 1.

Thus, as shown particularly in FIG. 2, the apparatus includes a housing, generally designated 20, formed with an inlet opening 21 through which the raw medical waste to be treated is introduced, and an outlet opening 22 through which the medical waste is removed after its treatment. A pivotal lid 23 overlies the inlet opening 21 and is pivotal, by a handle 24, either to its open position for introducing the raw medical waste, or to its closed position for closing the inlet opening 21. The outlet opening 22 receives a waste collector in the form of a drawer 25 normally disposed within housing 21 for collecting the medical waste after its treatment. Drawer 25 is pullable in the outer direction by grasping handle 26 in order to remove the treated medical waste for disposal.

As further shown in FIG. 2, housing 20 also includes a water supply pipe 27 for feeding water into the apparatus, an inlet opening 28 for introducing a supply of liquid disinfectant into a reservoir in the apparatus, and an outlet pipe 29 for removing liquid from the apparatus. The illustrated apparatus further includes an electrical cable 30 for supplying electrical power to the apparatus, and a control panel 31 for inputting various control parameters, producing various displays, and/or for outputting various data to printers, recorders, or other data processors.

As further shown in FIG. 2, the inlet opening 21 normally covered by the pivotal lid 23 is located in a slanted section 20a in the front wall of housing 20, to permit the convenient introduction of the raw medical waste to be treated. The outlet opening 22, occupied by the waste-removal drawer 25, is located in an underlying vertical section 20b of the front wall of housing 20 to permit the convenient removal and disposal of the medical waste after it has been treated.

The treatment of the medical waste is completely performed within housing 20. Such treatment includes a shredding operation in which the different types of wastes are shredded into a reduced-volume form, a mixing operation in which the shredded waste is mixed with water and a disinfectant, a packaging operation in which the disinfected waste is dumped into a filter bag, and a draining operation in which disinfected liquids are drained from the waste solids in the filter bag.

FIGS. 3 and 4 more particularly illustrate the internal structure of the apparatus for performing the foregoing operations.

Thus, as shown in FIG. 3, the housing 20 includes a treatment vessel, generally designated 40 (corresponding to vessel 2 in FIG. 1), in which all the foregoing operations are performed, except the final two operations, namely the packaging and draining operations which are performed in the waste-removal drawer 25. Treatment vessel 40 may be of any suitable configuration. As illustrated, it includes an upper section 41 of large cross-sectional area defined by four vertically-extending side walls 42, and a lower section 43 of smaller cross-sectional area defined by side walls 44 converging towards the bottom wall 45. The upper end 46 of the treatment vessel 40 is open.

Treatment vessel 40 is pivotal to a plurality of angular positions about a shaft 47 passing through the lower section 43. The treatment vessel is pivotted to any selected angular position by a suitable drive corresponding to positioning drive 7 in FIG. 1. FIG. 3 illustrates the drive as including a cylinder 48 pivotal at one end 48a to the bottom of housing 20, and a piston 49 receivable within the cylinder and pivotal at its opposite end 49a to the treatment vessel 40. It will be appreciated, however, that the positioning of the treatment vessel could be by any suitable drive, e.g., electric, hydraulic, water-operated, or pneumatic, as desired.

FIG. 3 illustrates the treatment vessel 40 in full lines in its vertical position 40a, i.e., with its longitudinal axis parallel to the vertical axis of housing 20, and with the open end 46 of the treatment vessel oriented vertically. This is the waste-treating position of the treatment vessel. Treatment vessel 40 may be pivotted about shaft 47 to a second position, shown in broken lines at 40b, wherein its open end, shown by broken lines 46b, is slanted upwardly and is aligned with the housing inlet 21 for introducing raw medical waste into the treatment vessel. Treatment vessel 40 is also pivotal to a third position, shown at 40c, wherein its open end, shown at 46c, is slanted downwardly and is aligned with the waste-removal drawer 25 in the outlet opening 22 of the housing, for dumping the medical waste after it was processed within the treatment vessel.

Shaft 47, which pivotally mounts treatment vessel 40, also serves as the coupling between the shredder (3, FIG. 1) within the treatment vessel and its drive (4, FIG. 1) externally of the treatment vessel. The shredder 3 within the treatment vessel 40 may be of any known construction for shredding or grinding the waste, such as in the above-cited U.S. Pat. No. 5,673,861, and therefore further details of its construction and operation are not set forth herein.

The apparatus illustrated in FIG. 3 further includes the compactor head 5 and the compactor motor 6 for reciprocating the compactor head in and out of the treatment vessel 40. Preferably, the side of compactor head 5 facing the treatment vessel 40 is of concave configuration. Drive 6 is controlled to reciprocate compactor head 5 only within the large-volume upper section 41 of the treatment vessel 40, so as not to engage the shredder 3 within the lower section 43 treatment vessel or the shaft 47 coupling it to its motor 4.

The waste-removal drawer 25 at the lower end of the housing 20 is manually movable, via its handle 26, to a closed position as illustrated in FIG. 2, or to an open position as illustrated in FIG. 3. FIG. 3 schematically illustrates the movements of drawer 25 guided by a telescopic guide rail 50, but it will be appreciated that any guiding arrangements may be used for this purpose. When drawer 25 is in its closed position (shown in FIG. 2), and the treatment vessel 40 is in its lowermost waste-removal position (shown by broken lines 40), the open end 46c of the treatment vessel is aligned with the interior of the drawer 25 to enable the drawer to receive the medical waste after having been processed as will be described more particularly below.

Drawer 25 is lined with a removable filter bag 51 for receiving the treated medical waste dumped from the treatment vessel 40. Preferably, the bottom wall of drawer 25 is slanted downwardly from the front side towards the rear side of the drawer, as shown at 52, and the filter bag 51 within the drawer is permeable to liquids, e.g., by being made of a non-woven filter material. Disinfected liquids within the processed medical waste dumped from treatment vessel 40 into the filter bag 51, thus drain by gravity out of the bag to the bottom 52 of drawer 25, and from an outlet 53, to the bottom of the housing 20 at the rear side of the housing. As shown in FIG. 3, the rear side of the housing may include a suction pump 54 (corresponding to suction pump 13, FIG. 1), and an outlet 55 for draining such liquids to the sewage system.

The water and the disinfectant are fed to the raw medical waste in the treatment vessel 40 at the time compactor head 5 and the shredder unit (3, FIG. 1), driven by motor 6, are operated to thoroughly shred and mix the medical waste with the water and disinfectant. Thus, as shown in FIG. 4, both the water supply line 27 and its control valve 8 are mounted at the upper end of the housing 20, and the water is fed via a feed line 60 passing through an opening in the compactor head 5 to a nozzle 61 carried by the compactor head. Nozzle 61 faces the open end 46 of treatment vessel 45 in the vertical position of the treatment vessel, which constitutes the waste treating position of the treatment vessel. The disinfectant reservoir 10, and its pump 11, are mounted in the front part of the housing 20, and the disinfectant is fed via a feed line 62 which passes through another opening in the compactor head 5 to another nozzle 63 also facing the open end of the treatment vessel 40 when in its upright position. Both the water feed line 60 and the disinfectant feed line 62 are sufficiently long and flexible so as to accommodate the reciprocatory movements of the compactor head 5 when it is reciprocated by its motor 6. Preferably a liquid solution disinfectant is used. Following is one example (the percentage of the active ingredients being by weight) of one disinfectant, called "Ster-Cid" (Reg. TM), supplied by CID Lines of Belgium, which may be used:

| Active ingredients: | % |
| --- | --- |
| Didecyl dimethyl ammonium chloride | 07.80 |
| Alkyl (50% C14, 40% C12, 10% C16) dimethyl benzyl ammonium chloride | 17.06 |
| Glutaraldehyde | 10.72 |
| Inert ingredients: | 64.42 |
| Total: | 100.00 |

Figure 5:
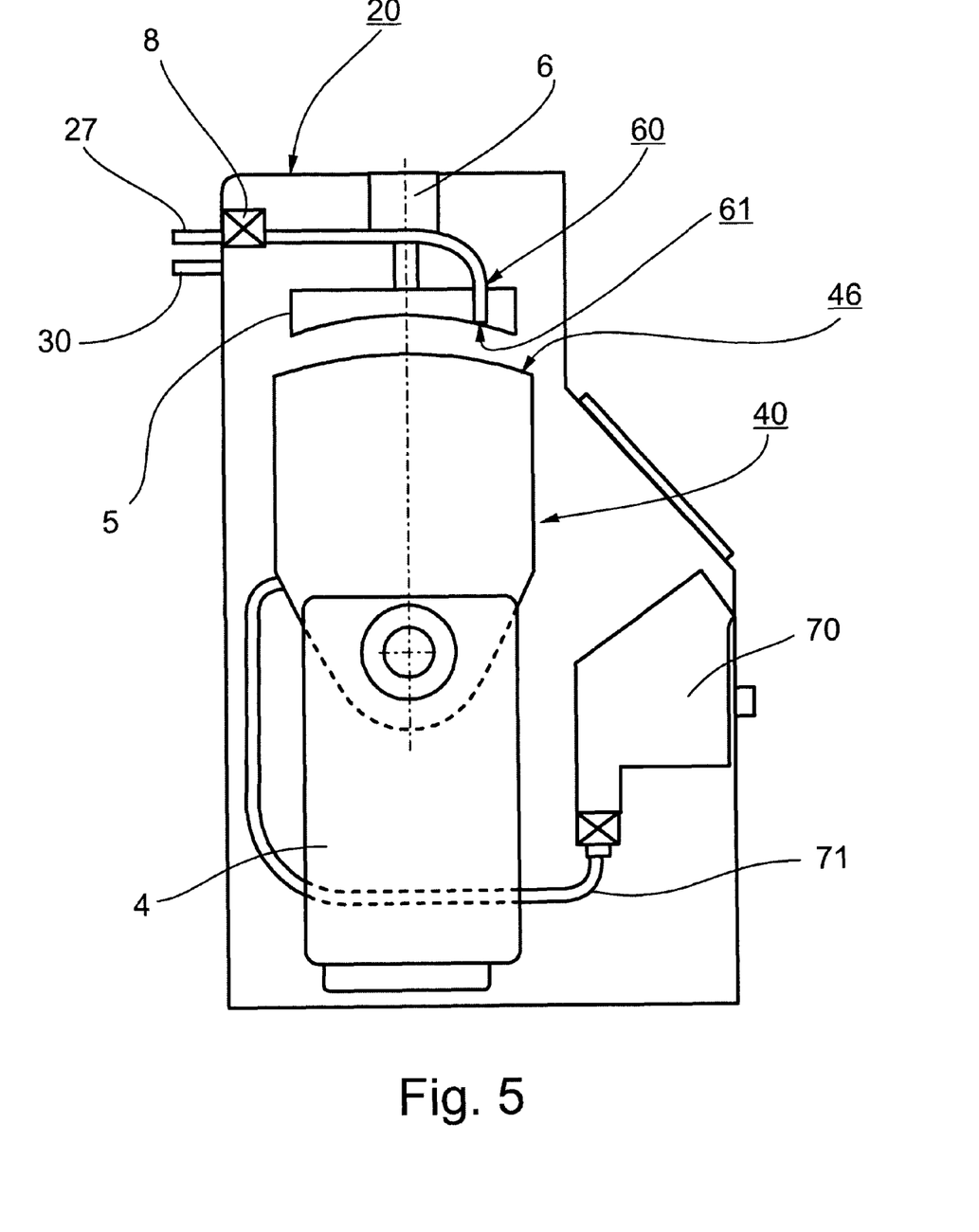
FIG. 5 is a view similar to that of FIG. 4 but illustrating a modification wherein the medical waste is disinfected by ozone.

Instead of using a liquid disinfectant, a gas disinfectant may be used, such as ozone. FIG. 5 illustrates a modification in the apparatus where ozone is used as a disinfectant. In this modification, the disinfectant reservoir 10 and pump 11 are omitted, and instead, the apparatus is provided with an ozone generator, generally designated 70, occupying the space of the disinfectant reservoir in FIG. 4. Ozone generator 70 generates ozone from the outside atmosphere and supplies the ozone via a feed line 71 directly to the treatment vessel 40 below the water level therein. When ozone is used as the disinfectant, the disinfectant opening 28 in the recess section 20c (FIG. 2) of the housing would be omitted. In all other respect, the apparatus illustrated in FIG. 5 would be constructed and operated in the same manner described above with respect to FIGS. 1–4, and therefore the same reference numerals have been used for corresponding parts to facilitate understanding.

Operation

The above-described apparatus may be operated as follows:

Initially, treatment vessel 40 would be in its loading position, shown in broken lines 40b in FIG. 3, wherein its open end 46 is aligned with the inlet opening 21 for introducing the raw medical waste to be disposed. In addition, drawer 25 in the outlet opening 22 of the housing would be in its inner position shown in FIG. 2.

Whenever waste is to be disposed, the user grasps handle 24 of pivotal lid 23 to open the inlet opening 21, and introduces the waste through that opening into the treatment vessel 40.

After the treatment vessel has thus received a charge of medical waste, the treatment vessel may be pivotted to its upright position 40b, shown in full lines in FIG. 3, which constitutes the waste-treating position of the treatment vessel. While in this position, the compactor head 5 is operated to compact the waste within the treatment vessel 40, and the shredder 3 (FIG. 1) within the treatment vessel (2, FIG. 1) is operated to shred the medical waste therein. At the same time, both water and disinfectant liquid are fed into the treatment vessel via the compactor head 5 such that the reciprocations of the compactor head and the operation of the shredder thoroughly shred the waste and thoroughly mix it with the water and disinfectant. After the medical waste has been shredded and mixed with the water and disinfectant, the treatment vessel 40 is then pivoted to its waste-removal position, shown by broken lines 40c in FIG. 3, to dump the waste into the filter bag 51 within the drawer 25. During this dumping operation, the shredder 3 could be operated in alternating directions in order to facilitate freeing the shredded waste from the shredder into the filter bag 5 within drawer 25.

As indicated earlier, the filter bag 51 is preferably liquid-permeable, and bottom wall 52 of drawer 25 is preferably inclined downwardly from the front end to the rear end of the drawer. This permits excess liquid within the shredded mixture to drain through the filter bag and through the drain outlet 53 in drawer 25 into the interior of the housing 20, where it is removed by section pump 54 and liquid drain line 29 to the sewage system. Drawer 25 may then be pulled open to enable removal of the filter bag 51 with the disinfected solids for disposition in any suitable manner.

When the disinfectant is ozone, as shown in the modification of FIG. 5, the treatment vessel 40 is preferably first filled with water before the ozone is introduced to assure that the ozone is well mixed in the water within the treatment vessel. For example, the treatment vessel 40 could first be filled with water followed by the lowering of the compactor head 5 before the ozone generator 70 is operated. Another option would be to first lower the compactor head 5 into the treatment vessel 40, fill the treatment vessel with water, and then operate the ozone generator.

All the foregoing operations may be controlled by the control unit 13. Thus, as shown in FIG. 1, the control unit 13 controls the positioning drive 7 to first position the treatment vessel in its initial waste loading position 40b (FIG. 3), then to its waste-treating position 40a shown in full lines in FIG. 3, and finally to its waste-removal position 40c.

When the treatment vessel is in its waste-treating position 40a (shown in full lines in FIG. 3), control unit 13 controls, via valve 9, the water supplied through supply line 27 and feed line 60 to the nozzle 61 carried by the compactor head 5. Control unit 13 also controls via pump 11, the supply of the disinfectant via feed line 62 to nozzle 63 also carried by the compactor head 5. Control unit 13 further controls electrical motor 4 driving the shredder 3 within the treatment vessel 2, and the compactor motor 6 for reciprocating the compactor head 5 within the treatment vessel.

After the foregoing treatment operations are completed, treatment vessel 40 is moved to its waste-removal position 40c to dump the mixture of the shredded waste, water and disinfectant, into the filter bag 51 within the waste-removal drawer 25 while the drawer is in its inner, closed position. At this time control unit 13 also actuates the suction pump 12 to pump into the sewage system the disinfected liquids which have drained from the disinfected solids within the bag 51, thereby decreasing the bulk of the disinfected solids within the bag 51 for disposal in any suitable manner.

The illustrated apparatus may include appropriate mechanical and/or electrical interlocks to assure proper operation of the apparatus. For example, the treatment vessel could include a mechanical interlock which permits the inlet opening cover 23 to be opened only when the treatment vessel is in the waste-loading position (40b, FIG. 3). It may include another interlock which permits the drawer 25 to be opened only when the treatment vessel is in the waste-removing position (40c, FIG. 3) to allow removal of the bagged waste, or in the waste-loading position (40l, FIG. 3) in order to allow insertion of a filter bag into the drawer. In addition, the control unit 14 may include electrical interlocks which permit the compactor head 5 to be reciprocated, the water to be fed, and the disinfectant to be fed, only when the treatment vessel is in the erect, waste-treating position 40a shown in full lines in FIG. 3. The shredder 3 may be controlled so as to be operative only in the waste-treatment position of the treatment vessel, or in the waste-removing position of the treatment vessel to enhance removal of the shredded waste. In addition, an electrical interlock may be provided to permit operation of the suction pump 13 only in the waste-removal position of the treatment vessel.

While the invention has been described particularly for disposing medical wastes, the invention could obviously be used in other waste-disposal applications, e.g., not requiring a disinfectant, etc. It will therefore be appreciated that, while the invention has been described above with respect to a preferred embodiment, this embodiment is set forth merely for purposes of example, and that many other variations, modifications and applications of the invention may be made.

What is claimed is:

1. Apparatus for treating waste to facilitate its disposition, comprising:
    a housing having an inlet for introducing the waste to be treated;
    a treatment vessel within said housing and having an open top for receiving and removing said waste, said treatment vessel being pivotal to a waste-loading position with its open top aligned with said housing inlet for receiving waste introduced therethrough, and to a waste-treating position for treating the waste within the treatment vessel;
    and a shredder within said treatment vessel for shredding waste therein before being removed from the treatment vessel.

2. The apparatus according to claim 1,
    wherein said housing also includes an outlet, separate from said inlet, for removing the waste after its treatment;
    and wherein said treatment vessel is also pivotal to a waste-removing position with its open top aligned with said housing outlet for removing therethrough the waste after treatment in the treatment vessel.

3. The apparatus according to claim 2, wherein said apparatus further includes a control system which permits operation of the shredder when the treatment vessel is in said waste-treating position and also when the treatment vessel is in said waste-removing position to facilitate removal of the shredded waste from the treatment vessel.

4. The apparatus according to claim 1, wherein said treatment vessel has an upper section of large cross-sectional area, and a lower section of a cross-sectional area which decreases towards the bottom of the treatment vessel; said shredder being located in said lower section of the treatment vessel.

5. The apparatus according to claim 1, wherein said shredder is driven by a drive within the housing and coupled to the shredder within the treatment vessel by a shaft passing through a side wall of the treatment vessel; said treatment vessel being pivotally mounted about said shaft.

6. The apparatus according to claim 5, wherein said treatment vessel is pivotally mounted by an extensible-retractable piston-cylinder unit coupled at one end to the housing and at the opposite end to said treatment vessel.

7. The apparatus according to claim 1, wherein said waste-treating position is one wherein the longitudinal axis of the treatment vessel is aligned with the vertical axis of said housing, with the open end of the treatment vessel facing upwardly.

8. The apparatus according to claim 1, wherein the apparatus further comprises:
    a compactor head aligned with said open end of the treatment vessel when the treatment vessel is in said waste treating position so as to be reciprocatable within the treatment vessel to compact the waste therein;

and a control system permitting operation of said compactor head only when the treatment vessel is in its waste-treating position.

9. The apparatus according to claim 8, wherein said apparatus further comprises:

a water supply line feeding water into the treatment vessel to be mixed with the waste therein during the operation of said compactor head and shredder.

10. The apparatus according to claim 9, wherein said water supply line feeds water into the treatment vessel via said compactor head so as to be mixed with the waste within the treatment vessel during the reciprocations of said compactor head within the treatment vessel.

11. The apparatus according to claim 10, wherein said apparatus further comprises:

a feed line for feeding a disinfectant into said treatment vessel to be mixed with the waste and the water during the operation of said compactor head.

12. The apparatus according to claim 11, wherein said feed line feeds a liquid disinfectant into said treatment vessel via said compactor head so as to be mixed with the waste and the water within the treatment vessel during the operation of said compactor head.

13. The apparatus according to claim 11, wherein said feed line feeds ozone directly into said treatment vessel during the operation of said compactor head.

14. Apparatus for treating waste to facilitate its disposition, comprising:

a housing having an inlet for introducing the waste to be treated, and an outlet for removing the waste after its treatment;

a treatment vessel within said housing and having an open top for receiving and removing said waste, said treatment vessel being pivotal to a waste-loading position with its open top aligned with said housing inlet for receiving waste introduced therethrough, and to a waste-removing position with its open top aligned with said housing outlet for removing therethrough the waste after treatment in the treatment vessel;

and a shredder within said treatment vessel for shredding waste therein before being removed from the treatment vessel through said housing outlet.

15. The apparatus according to claim 14, wherein said treatment vessel is also pivotal to a third position, constituting a waste-treating position, said shredder being actuatable when the treatment vessel is in said waste-treating position.

16. The apparatus according to claim 14, wherein the housing outlet is occupied by a waste-removal drawer normally in an inner position aligned with said open end of the treatment vessel when the treatment vessel is in its waste-removing position to receive the waste therefrom, but is movable outwardly to enable removal of the waste from the drawer.

17. The apparatus according to claim 16, wherein said waste-removal drawer has a bottom which is slanted downwardly from its outer side toward its inner side to permit liquid in the treated waste to separate from the solids, and to drain towards the inner side of the drawer, said drawer including an outlet opening at its inner side to drain the liquid therefrom.

18. The apparatus according to claim 17, wherein the liquid drains from the waste-removal drawer to the bottom of said housing, and the bottom of said housing also includes an outlet for outletting the liquid therefrom.

19. The apparatus according to claim 18, wherein said waste-removal drawer is lined with a filter bag which is liquid permeable to permit draining liquids from the solid wastes contained in the filter bag to the bottom of said housing.

20. The apparatus according to claim 19, wherein said apparatus further includes a suction pump for pumping liquids from the bottom of said housing through said housing outlet.

* * * * *